(12) United States Patent
Schwaegerle et al.

(10) Patent No.: US 10,441,162 B2
(45) Date of Patent: Oct. 15, 2019

(54) OPHTHALMIC EXAMINATION SUITE HAVING CHAIR WITH SIDEWARD MOVEMENT

(71) Applicant: RELIANCE MEDICAL PRODUCTS, INC., Mason, OH (US)

(72) Inventors: Gary G. Schwaegerle, Cincinnati, OH (US); Michael A. Carvajal, Chicago, IL (US); Deepak Sridhara, Mason, OH (US)

(73) Assignee: RELIANCE MEDICAL PRODUCTS, INC., Mason, OH (US)

( * ) Notice: Subject to any disclaimer, the term of this patent is extended or adjusted under 35 U.S.C. 154(b) by 0 days.

(21) Appl. No.: 15/213,043

(22) Filed: Jul. 18, 2016

(65) Prior Publication Data

US 2016/0324415 A1    Nov. 10, 2016

Related U.S. Application Data

(63) Continuation of application No. 13/655,917, filed on Oct. 19, 2012, now Pat. No. 9,392,937.

(60) Provisional application No. 61/548,964, filed on Oct. 19, 2011.

(51) Int. Cl.
*A61B 3/00* (2006.01)
*A61G 5/00* (2006.01)

(52) U.S. Cl.
CPC .......... *A61B 3/0083* (2013.01); *A61B 3/0075* (2013.01); *A61G 5/00* (2013.01)

(58) Field of Classification Search
CPC ........ A61B 3/103; A61B 3/145; A61B 3/152; A61B 3/032; A61B 3/107; A61B 3/10; A61B 3/0025; A61B 3/14; A61B 3/12; A61B 3/113; A61B 3/102; A61B 3/0091; A61B 3/0041; A61B 3/0058; A61B 3/1015; A61B 3/0033; A61B 3/112; A61B 3/0008
USPC .................. 351/225, 244, 245, 246
See application file for complete search history.

(56) References Cited

U.S. PATENT DOCUMENTS

| | | | | |
|---|---|---|---|---|
| 4,741,506 A | * | 5/1988 | Schwaegerle | A61G 15/10 248/430 |
| 5,580,023 A | * | 12/1996 | Burton | A61B 3/18 248/430 |
| 6,106,065 A | * | 8/2000 | Carroll | A47C 1/0347 297/325 |
| 8,936,315 B2 | * | 1/2015 | Fienup | A61B 3/024 297/330 |
| 2008/0079252 A1 | * | 4/2008 | Shutter | A61G 3/0808 280/755 |
| 2010/0066111 A1 | * | 3/2010 | Fritsche | A61G 3/061 296/1.07 |
| 2010/0112513 A1 | * | 5/2010 | Frojdman | A61G 15/00 433/33 |
| 2012/0292883 A1 | * | 11/2012 | Noonan | A61G 5/006 280/304.1 |

* cited by examiner

*Primary Examiner* — Evan P Dzierzynski
*Assistant Examiner* — Sharrief I Broome
(74) *Attorney, Agent, or Firm* — Taft Stettinius & Hollister LLP; Derek B. Lavender; Ryan O. White (57) ABSTRACT

An ophthalmic examination suite including a base support having a base plate, a carriage movable on the base plate, the carriage being laterally movable between a first position and a second position relative to an instrument delivery stand, and a chair coupled to the carriage, the chair being configured to receive a seated patient thereon.

20 Claims, 11 Drawing Sheets

OPHTHALMIC EXAMINATION SUITE HAVING CHAIR WITH SIDEWARD MOVEMENT

CROSS-REFERENCE TO RELATED APPLICATIONS

This application is a continuation of U.S. patent application Ser. No. 13/655,917 filed Oct. 19, 2012, which in turn claims the benefit of U.S. Provisional Patent Application Ser. No. 61/548,964, filed Oct. 19, 2011, the complete disclosures of which are hereby expressly incorporated in their entireties herein by this reference.

TECHNICAL FIELD

The present invention generally relates to ophthalmic examination suites, such as those used during an eye examination. More particularly, the invention relates to moveable examination chairs used in eye examination procedures.

BACKGROUND OF THE DISCLOSURE

During an eye examination, a series of tests are performed on a patient, who is typically seated in an examination chair. These tests can include an external examination of the eyes and surrounding tissues, tests to determine the acuteness or clearness of vision, examination of the pupils, and other examinations, tests or procedures pertaining to the eyes. Instruments are used during the eye examination and these instruments are typically retrieved from or stored on an associated instrument delivery stand positioned nearby the seated patient. For example, instrument delivery stands are known that include an instrument arm for presenting and positioning a table supporting an examination instrument in front of a patient. For example, a slit lamp machine may be supported on a table connected with an instrument arm, and is used by an eye doctor or other examiner to view different parts of the eye, including the cornea, the iris, the optic nerve, the retina, and the like.

Because of natural variations in the size and shape of patients, an instrument arm ought to have features providing position-adjusting capabilities in order to appropriately position an examination instrument with respect to a patient. For example, a child may be significantly shorter than an average height adult, so an instrument arm should be able to position the examination instrument at a child-appropriate height. In addition, a heavyset patient will be positioned differently in an examination chair than a small-framed patient, and an instrument arm should be able to position the examination instrument appropriately in either case.

Moreover, examination of wheelchair-bound patients presents other issues related to the presentation and positioning of examination instruments. In some circumstances, for example, a conventional examination chair must be moved to make room for patient in a wheelchair. An instrument arm should be able to position an examination instrument, such as a slit lamp machine, appropriately with respect to a wheelchair-bound patient. This may be challenging, however, if an examination room is not sufficiently large to easily accommodate the modifications necessary for the examination. For example, it may not be possible to completely remove a conventional examination chair, as they are typically very large and heavy. In other circumstances, the positional adjustability of the instrument arm may be insufficient to appropriately position the examination instrument with respect to a wheelchair-bound patient.

There is a need, therefore, for an ophthalmic examination suite that addresses one or more of the needs in the field of ophthalmic examination apparatus and provides for appropriate positioning of an examination instrument with respect to a patient, including when the patient is wheelchair bound.

SUMMARY OF THE INVENTION

In accordance with one embodiment, an ophthalmic examination suite is provided and includes a base support having a base plate, a carriage movable on the base plate, the carriage being laterally movable between a first position and a second position relative to an instrument delivery stand, and a chair coupled to the carriage, the chair being configured to receive a seated patient thereon.

In accordance with another embodiment, a method of configuring an ophthalmic examination suite to facilitate examining a patient in a wheelchair is provided. In accordance with this embodiment, the ophthalmic examination suite includes a base support having a base plate, a carriage movable on the base plate, and a chair coupled to the carriage. The method comprises creating a space lateral and adjacent to the chair by moving the carriage to a position generally adjacent to an instrument delivery stand, and moving a wheelchair into the space.

Other objects and benefits of the disclosure will become apparent from the following written description along with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF THE ILLUSTRATIVE EMBODIMENTS

Referring now to the figures, an exemplary eye examination suite in accordance with the principles of the present invention is shown and is indicated generally by the numeral 10. The eye examination suite 10 is of the type used for examinations and includes an instrument delivery stand 12, a chair 14 for a patient to sit in, and a base 16. The stand 12 and the chair 14 are connected through the base 16, as shown in the figures. During an eye examination, a patient may be seated in the chair 14 in a forward-facing direction, and an eye doctor or other practitioner may stand or be seated on a stool (not shown) generally in the region near the patient in the chair 14 and the stand 12.

Figure 1:
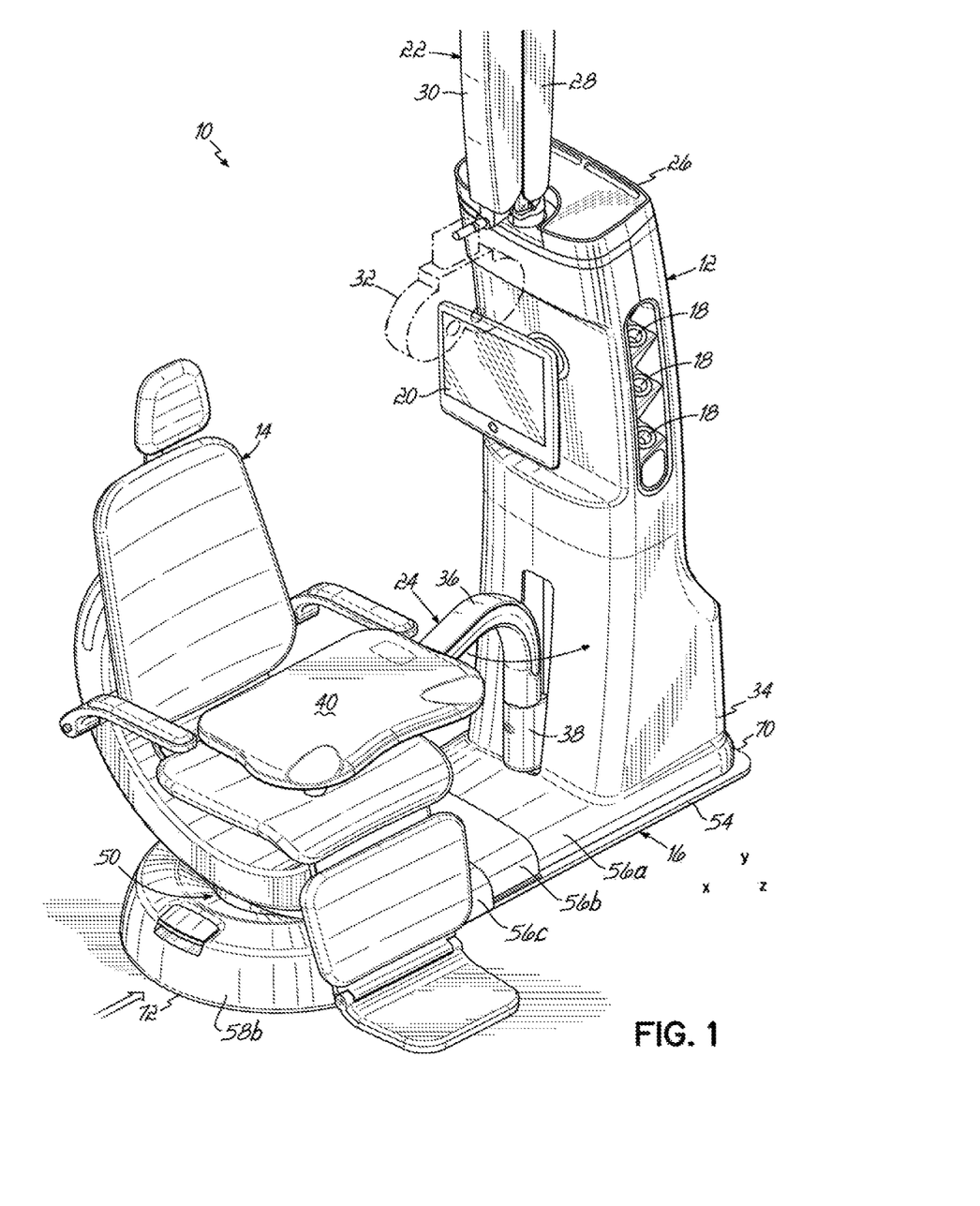
FIG. 1 is an isometric view of an eye examination suite.

As shown in FIG. 1, the stand 12 provides storage 18 for examination instruments, supports an information screen 20, and includes an upper instrument arm assembly 22 and a lower instrument arm assembly 24. The upper instrument arm assembly 22 extends from an upper region 26 of the stand 12 and includes a first arm portion 28, a second arm portion 30, and a phoropter 32. The first arm portion 28 is adjustably connected with the stand 12, and the second arm portion 30 is adjustably connected with the first arm portion 28. In addition, the phoropter 32 is adjustably connected with the second portion 30. Through these adjustable connections, the upper instrument arm assembly 22 is adjustable with respect to a seated patient and allows the physician or practitioner to position the phoropter 32 appropriately with respect to the patient's face and eyes as part of an eye examination. The upper instrument arm assembly 22 can also be placed into a stored position adjacent the stand 12, as shown in FIG. 1.

Figure 4A:
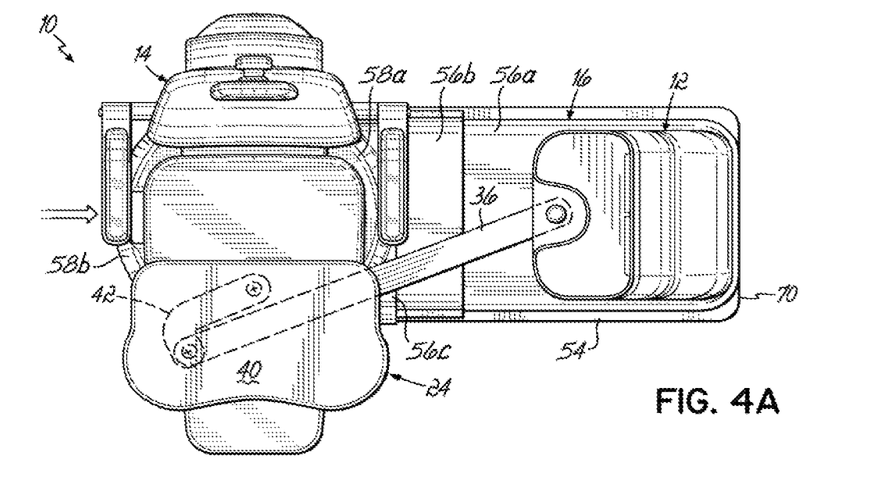
FIG. 4A is a top plan view of the eye examination suite shown in FIG. 1, with the chair in an examination position.
Figure 4B:
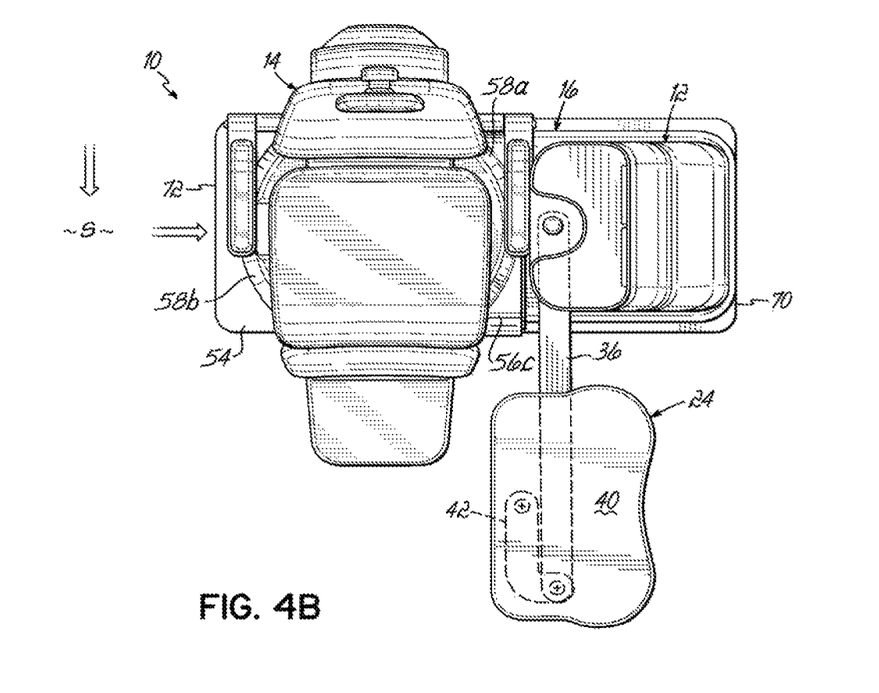
FIG. 4B is a top plan view similar to FIG. 4A, with the chair moved toward the instrument delivery stand and the lower instrument arm assembly rotated away from the chair.
Figure 4C:
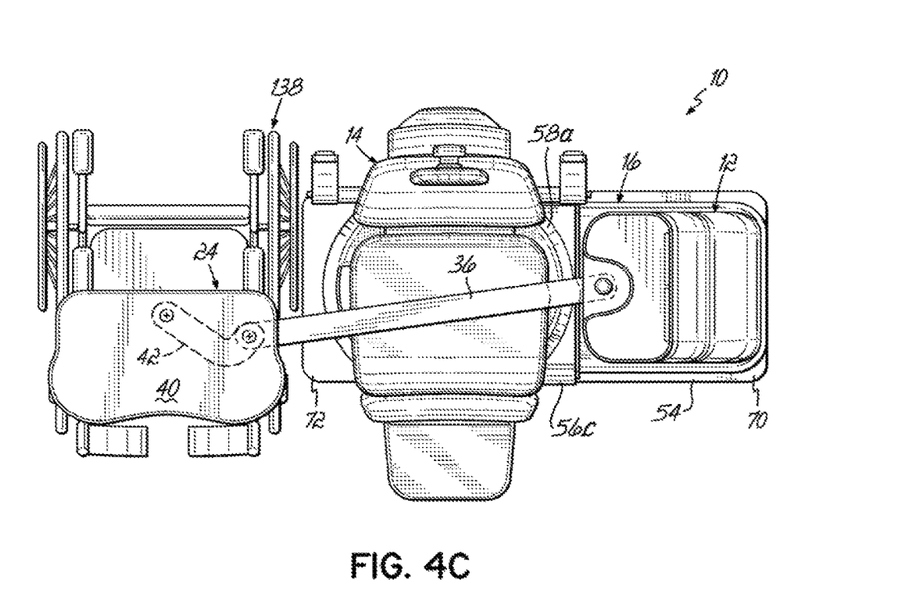
FIG. 4C is a top plan view of the eye examination suite shown in FIG. 1, with the chair moved toward the instrument delivery stand and a wheelchair situated in a space next to the chair.

The lower instrument arm assembly 24 extends from a lower region 34 of the stand 12 and includes an arm 36 extending upwardly from a support 38, an instrument supporting element (such as a table 40), and a linkage 42 (as shown in FIGS. 4A, 4B, and 4C). The arm 36 is adjustably connected with the support 38, and the table 40 is adjustably connected with the arm 36 by the linkage 42. For example, the arm 36 is pivotably rotatable with respect to the support 38. The adjustable connection between the arm 36 and the table 40 is discussed further, below. Optionally, the arm 36 may be raised or lowered with respect to the base 16, such as by raising or lowering the support 38. Through these adjustable connections, the lower instrument arm assembly 24 is adjustable with respect to a seated patient and allows the physician or practitioner to position the table 40 (or any other instrument supporting element) appropriately with respect to the patient as part of an eye examination.

The linkage 42 is further described in U.S. patent application Ser. No. 13/655,898, filed on even date herewith, the disclosure of which is incorporated herein by reference.

In addition, the examination suite 10 provides for sideward movement of the chair 14 toward and away from the instrument delivery stand 12, as will now be described. Sideward movement of the chair 14 as shown and described herein is advantageous for making room in the examination suite 10 for a wheelchair to be positioned in an examination position.

Referring next to FIGS. 5-8, the chair 14 is supported by a base support 50 which, in turn, is supported on a moveable carriage 52. As will be apparent from the following description, the carriage 52 allows the chair 14 to be moved toward and away from the instrument delivery stand 12 on the base 16.

Figure 2:
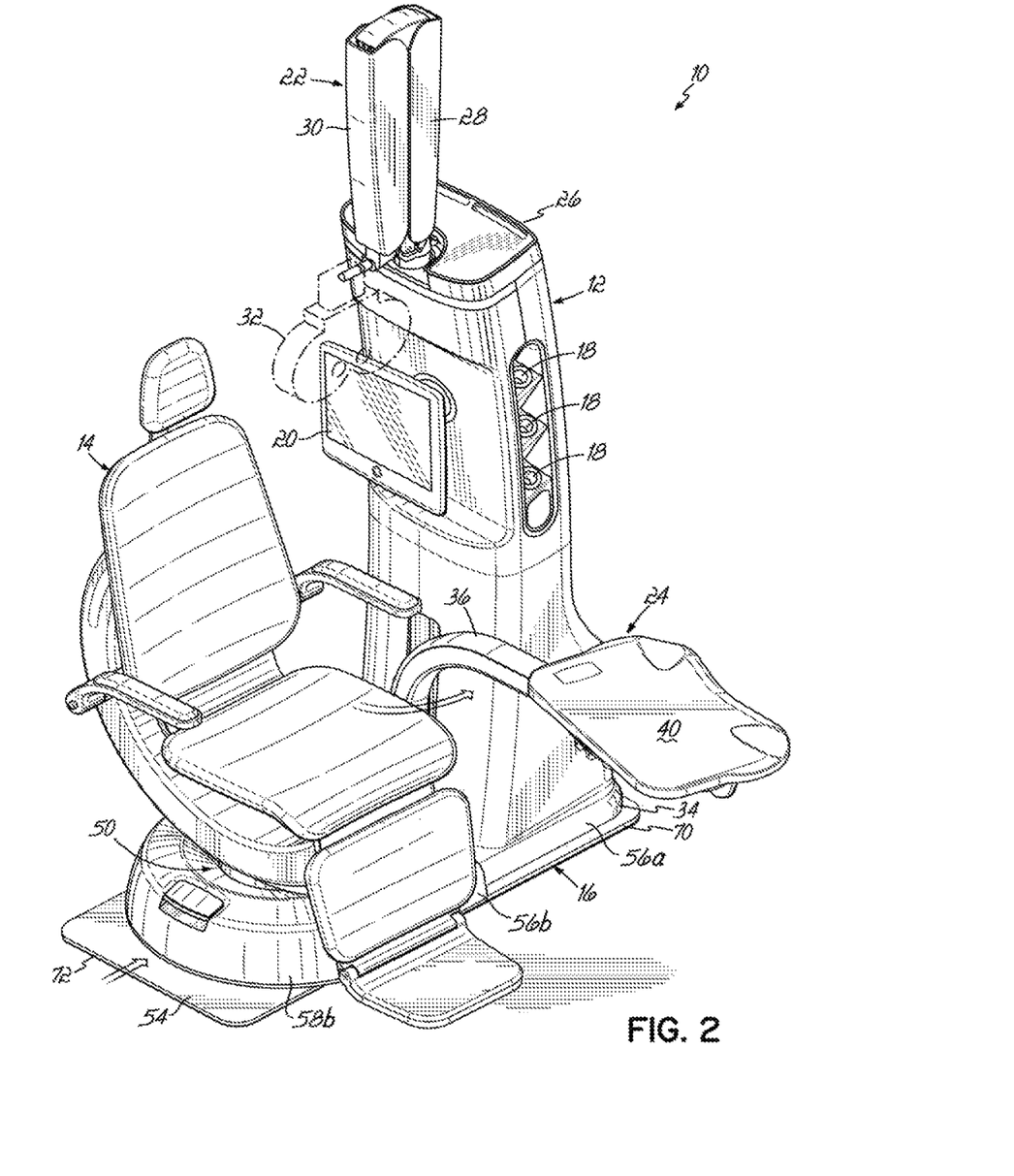
FIG. 2 is a further isometric view of the eye examination suite of FIG. 1, with the chair moved toward the instrument delivery stand and the lower instrument arm assembly rotated away from the chair.
Figure 3:
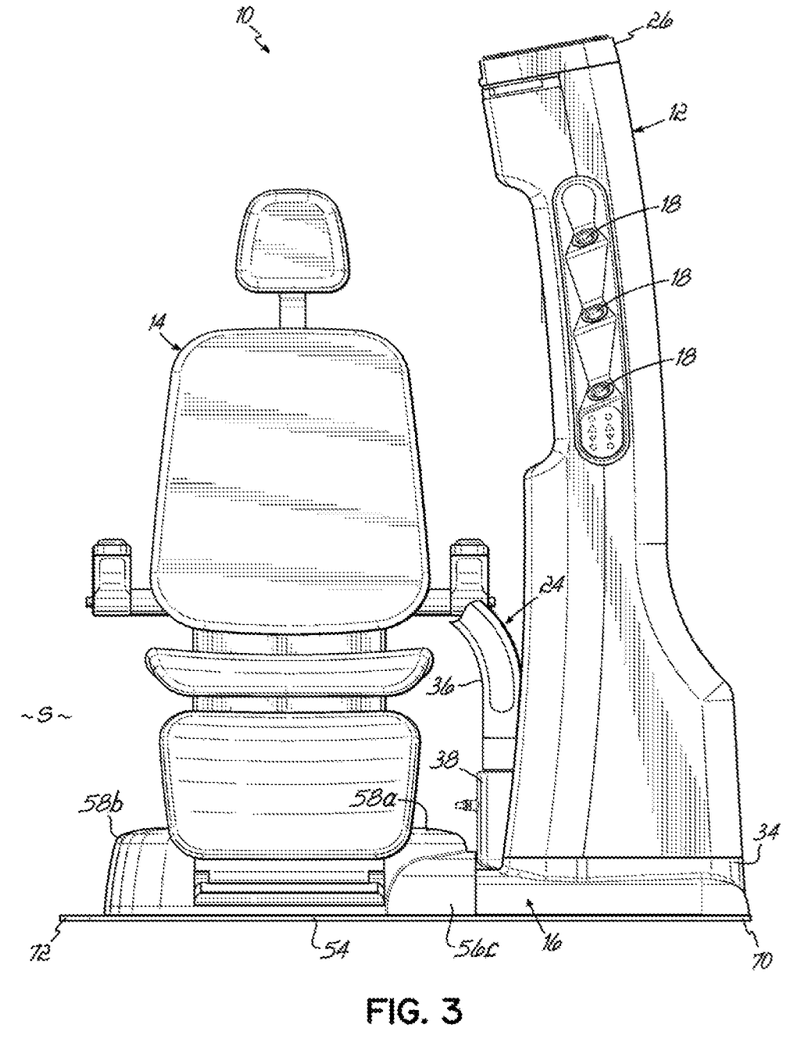
FIG. 3 is a front elevation view showing the configuration of FIG. 2, with portions of the lower instrument arm assembly and the upper instrument arm assembly removed for clarity.

In particular, the base 16 includes a base plate 54 and a plurality of base covers 56a, 56b, 56c that cover underlying components, including much of the base plate 54. The carriage 52 is moveable with respect to the base plate 54, and the base covers 56a, 56b, 56c cooperate to accommodate movement of the chair 14. For example, the base covers 56a and 56b slide and nest under the base cover 56c when the chair 14 is moved toward the instrument delivery stand 12 (as shown in FIGS. 2 and 3), and return to a generally side-by-side arrangement when the chair 14 is moved away from the instrument delivery stand 12 (as shown in FIG. 1). Therefore, it is not necessary to remove any of the base covers 56a, 56b, 56c before moving the chair 14 toward the instrument delivery stand 12. Nor is it necessary to replace any of the base covers 56a, 56b, 56c after moving the chair 14 away from the instrument delivery stand 12. In addition, base support covers 58a, 58b are positioned below the chair 14 and cover underlying components, including much of the base support 50 and the carriage 52.

Figure 6:
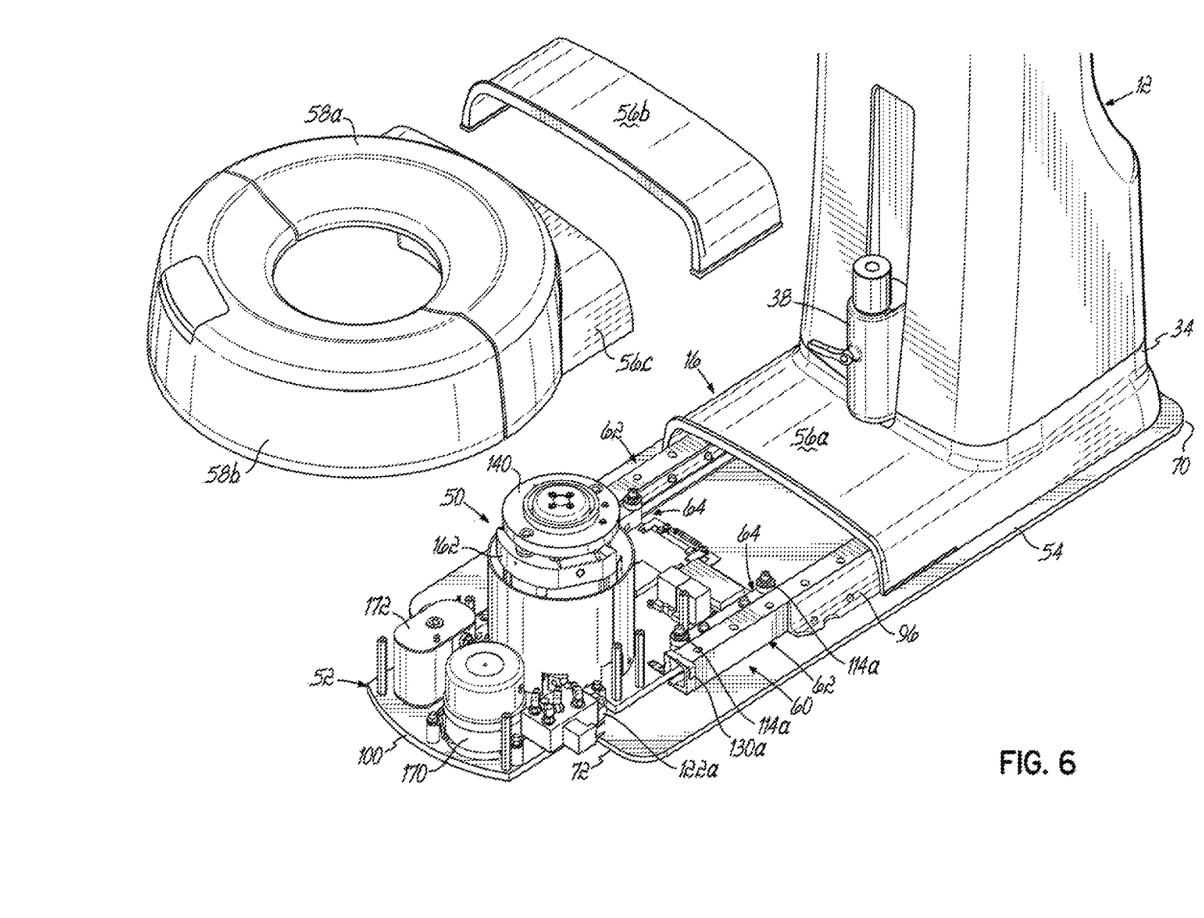
FIG. 6 is a partially disassembled view of the examination suite of FIG. 5 illustrating features of a track and guide assembly.
Figure 7A:
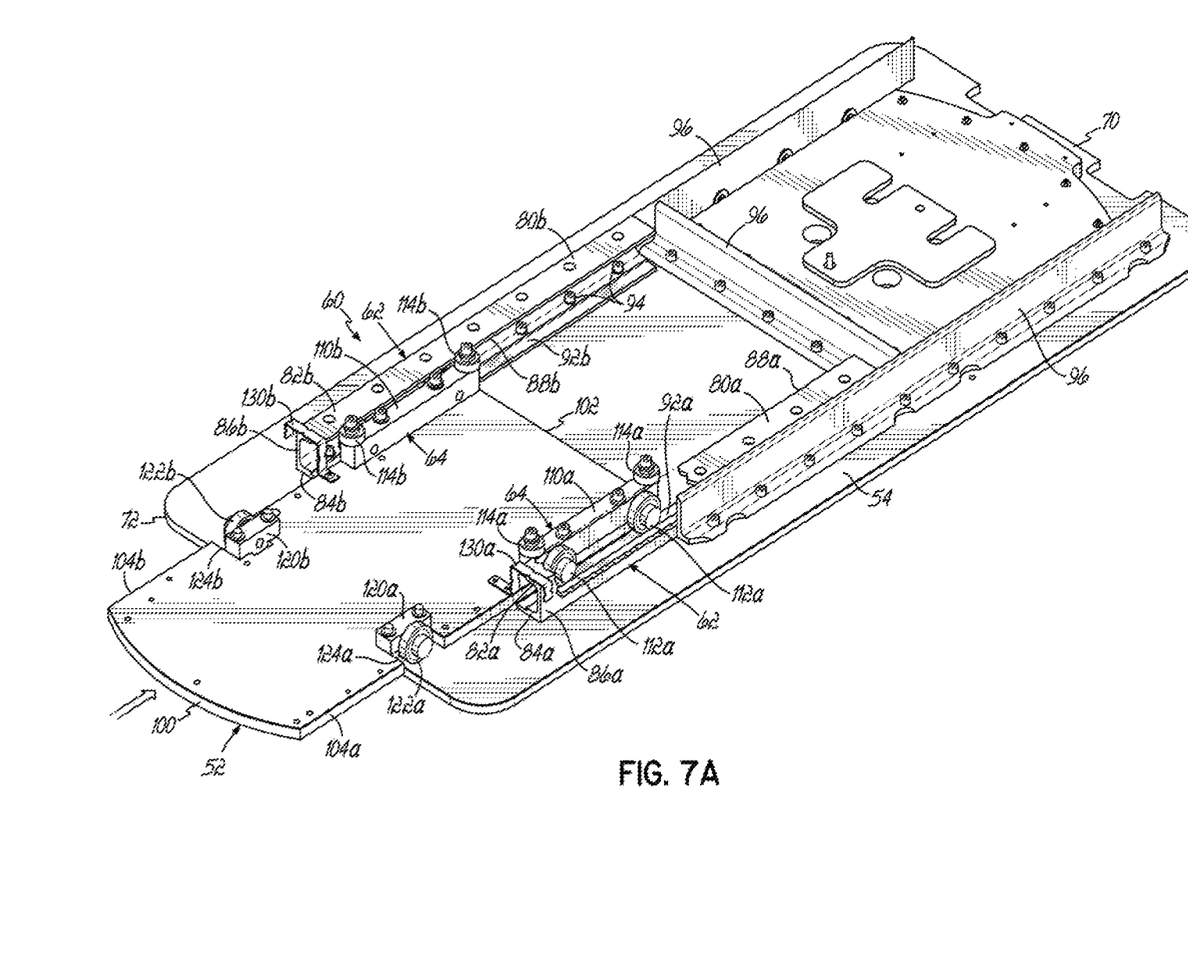
FIG. 7A is an isometric view of a base portion of the examination suite of FIG. 5 with the base support and various other components removed for clarity to illustrate features of a track and guide assembly.
Figure 7B:
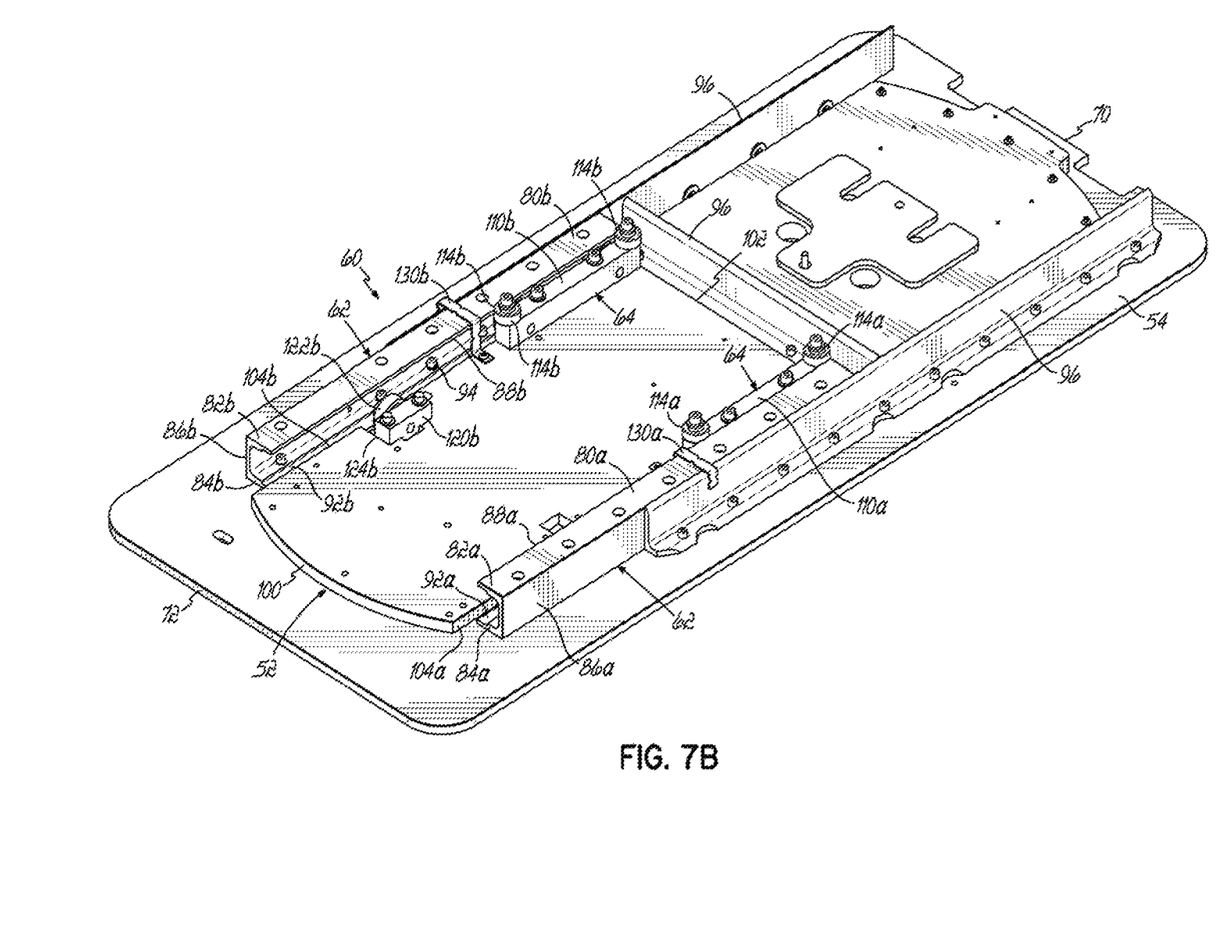
FIG. 7B is an isometric view similar to FIG. 7A but with the carriage moved toward a stand end of the base plate.

With particular reference to FIGS. 6, 7A, and 7B, a track and guide assembly 60 provides movement of the chair 14 with respect to the base plate 54. In particular, and in the embodiment shown, a track assembly 62 is associated with, or coupled with, the base plate 54 and a guide assembly 64 is associated with, or coupled with, the carriage 52. The track assembly 62 and the guide assembly 64 cooperate to provide movement of the carriage 52, and therefore the chair 14, which is supported by the base support 50 on the carriage 52. It will be appreciated that the track assembly could alternatively be associated with, or coupled with, the carriage 52, and the guide assembly with the base plate 54.

In the embodiment shown, the base plate 54 has a generally rectangular and planar shape and extends between a stand end 70 and a chair end 72. The instrument delivery stand 12 extends upwardly from base plate 54 generally in the vicinity of the stand end 70 (as shown in FIG. 3). The chair 14 is generally moveable with respect to the base plate 54 (on the carriage 52) between positions generally in the vicinity of the chair end 72 and intermediate the chair end 72 and the stand end 70 (as shown in FIGS. 4A and 4B). The base plate 54 may be fixedly attached to an underlying floor surface, such as by bolts or other fasteners.

Figure 8:
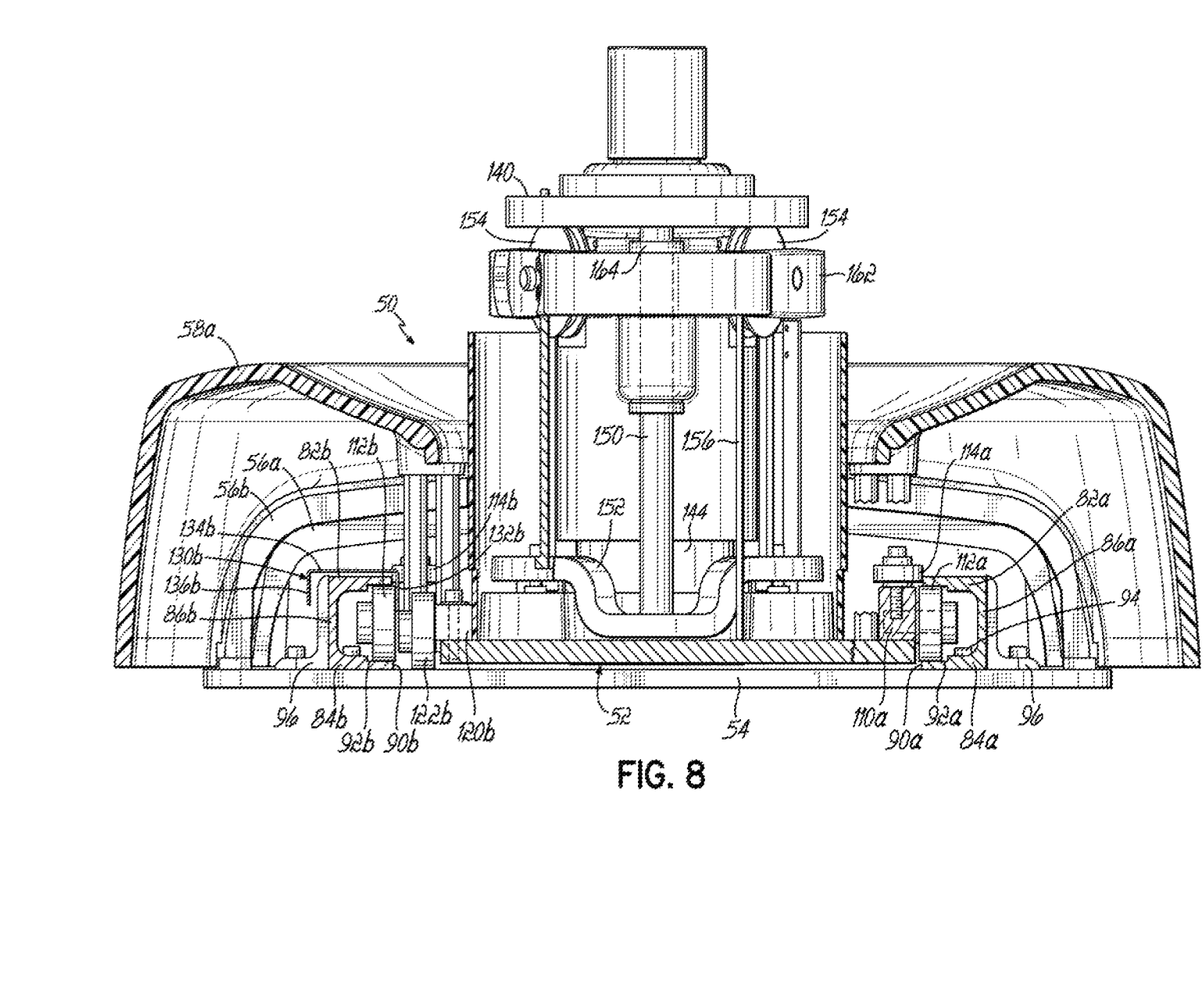
FIG. 8 is a cross-sectional view taken generally along line 8-8 in FIG. 5.
Figure 9:
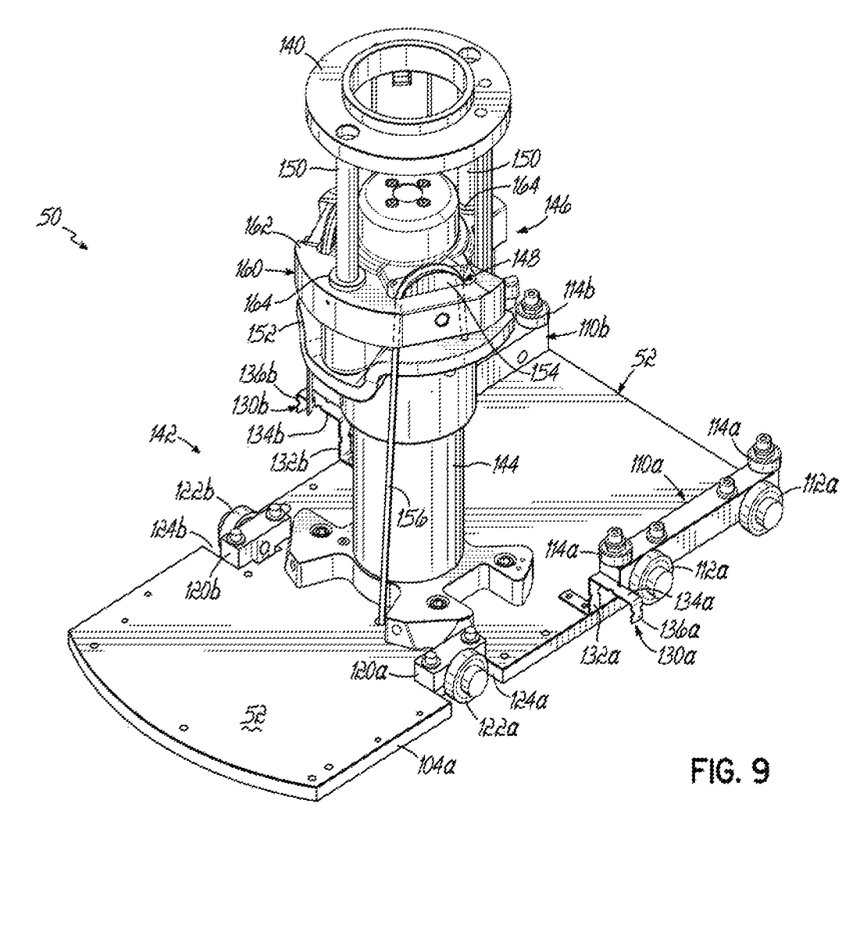
FIG. 9 is an isometric view of a support base of the examination suite of FIG. 5.

The track assembly 62 includes substantially similar track rails 80a, 80b mounted on the base plate 54. In particular, the track rails 80a, 80b extend generally parallel with one another intermediate the stand end 70 and the chair end 72. The track rails 80a, 80b have a generally c-shaped cross-section. In particular, each rail 80a, 80b includes respective upper arms 82a, 82b and lower arms 84a, 84b, which are connected by webs 86a, 86b, with the arms 82a, 82b, 84a, 84b and webs 86a, 86b defining a c-shape when viewed in cross section (as shown in FIG. 8). In addition, the c-shape of each of the track rails 80a, 80b opens, or faces, toward the other of the track rails 80a, 80b, so as to define facing upper inner surfaces 88a, 88b on the upper arms 82a, 82b and facing lower inner surfaces 90a, 90b on the lower arms 84a, 84b (as shown in FIGS. 7A and 8).

The upper arms 82a, 82b and the lower arms 84a, 84b extend generally parallel with the major plane of the base plate 54, while the webs 86a, 86b extend generally perpendicularly with the major plane of the base plate 54. The upper and lower arms 82a, 84a and 82b, 84b each define a respective track portion 92a, 92b of each track rail 80a, 80b.

The track portions 92a, 92b each receive one or more members of the guide assembly 64, as will be explained further below. The track rails 80a, 80b are attached to the base plate 54 by fasteners 94. Further, anchor rails 96 may be provided to support the connection between the track rails 80a, 80b and the base plate 54. The anchor rails 96 are positioned generally adjacent to and connected with the track rails 80a, 80b, and are also connected with the base plate 54.

The carriage 52 has a generally rectangular and planar shape and extends between a first, free end 100 and a second, captive end 102, and has first and second side surfaces 104a, 104b extending between the free and captive ends 100, 102. The carriage 52 is partially received between the track rails 80a, 80b, so that portions of the side surfaces 104a, 104b proximate the captive end 102 are received between the track rails 80a, 80b. In particular, and as shown in the figures, the captive end 102 of the carriage 52 is positioned between the track rails 80a, 80b, whereas the free end 100 of the carriage 52 extends beyond the track rails 80a, 80b, and in some configurations beyond the chair end 72 of the base plate 54 (as shown in FIGS. 6 and 7B). The first side surface 104a is positioned generally adjacent with and extends along the track rail 80a, and the second side surface 104b is positioned generally adjacent with and extends along the track rail 80b. The carriage 52 is moveable with respect to the base plate 54 in a sideward direction toward and away from the stand end 70 of the base plate 54.

The guide assembly 64 cooperates with the track assembly 62 to provide for movement of the carriage 52 relative to the base plate 54. The guide assembly 64 includes a plurality of guides, which in the embodiment shown include wheels, for facilitating the movement of the carriage 52. In particular, a plurality of vertically and horizontally-oriented wheels are connected with the carriage 52, and rollingly engage with either the base plate 54 or the track assembly 62 during movement of the carriage 52. As used herein, the term "vertically-oriented wheels" refers to those wheels that rotate about a substantially horizontal rotation axis, while the term "horizontally-oriented wheels" refers to those wheels that rotate about a substantially vertical rotation axis. It will be appreciated, however, that the guide assembly could alternatively include guides other than wheels, such as other friction-reducing structures.

As best seen in FIGS. 7A and 7B, guide member mounting blocks 110a, 110b are connected with the carriage 52 near its captive end 102 and extend generally along the first and second side surfaces 104a, 104b. Each guide member mounting block 110, 110b supports a pair of vertically-oriented wheels 112a, 112b and a pair of horizontally-oriented wheels 114a, 114b, all of which are free to rotate relative to the guide member mounting blocks 110a, 110b. As best seen in FIG. 8, the vertically-oriented wheels 112a, 112b are received in the track portions 92a, 92b, respectively, of the track rails 80a, 80b and facilitate movement of the carriage 52 with respect to the base plate 54. In particular, the wheels 112a, 112b rollingly engage with the track portions 92a, 92b when the carriage 52 is moved toward and away from the stand end 70 of the base plate 52. Also best seen in FIG. 8, the horizontally-oriented wheels 114a, 114b engage the upper inner surfaces 88a, 88b of the upper arms 82a, 82b and further facilitate movement of the carriage 52 with respect to the base plate 54. In particular, the wheels 114a, 114b rollingly engage with the upper inner surfaces 88a, 88b when the carriage 52 is moved toward and away from the stand end 70 of the base plate 52.

The configuration of the vertically and horizontally-oriented wheels 112a, 112b, 114a, 114b and the track rails 80a, 80b generally tends to prevent rotation of the carriage 52 relative to the base plate 54, such as may be encountered when a patient takes a seat in, or moves about in, the chair 14. In particular, the fit of the vertically-oriented wheels 112a, 112b in the track portions 92a, 92b of the rails 80a, 80b and the fit of the horizontally-oriented wheels with respect to the upper arms 82a, 82b of the track rails 80a, 80b generally tends to prevent rotation of the carriage 52 relative to the base plate 54.

Further, guide member mounting blocks 120a, 120b are connected with the carriage 52 intermediate the captive end 102 and the free end 100 and support vertically-oriented wheels 122a, 122b, which are free to rotate relative to the guide member mounting blocks 120a, 120b. The guide member mounting blocks 120a, 120b are positioned in notches 124a, 124b formed in the carriage 52 so that the wheels 122a, 122b are also positioned within the notches 124a, 124b and do not extend beyond the side surfaces 104a, 104b (as shown in FIG. 8). The wheels 122a, 122b are positioned so as to rotate between the track rails 80a, 80b, and as seen best in FIGS. 7B and 8, to rollingly engage with the base plate 54 when the carriage 52 is moved toward and away from the stand end 70 of the base plate 52.

As best seen in FIG. 8, the vertically-oriented wheels 112a, 112b, 122a, and 122b support the carriage 52 a slight distance above the base plate 54. Thus, when the carriage 52 is moved with respect to the base plate 54, the carriage 52 and the base plate 54 do not directly touch and the various wheels facilitate movement of the carriage 52 with respect to the base plate 54.

Optionally, and as shown in FIGS. 6-8, generally u-shaped support brackets 130a, 130b can be provided for support of electrical cables associated with the base support 50. Each support bracket 130a, 130b is mounted to the carriage 52 includes a first arm section 132a, 132b extending upwardly from the carriage 52, a second arm section 134a, 134b extending from the first arm section and over a respective upper arm 82a, 82b of the track rails 80a, 80b, and a third arm section 136a, 136b extending downwardly from the second arm section along the webs 86a, 86b of the track rails 80a, 80b.

The chair 14 is therefore moveable toward and away from the instrument delivery stand 12. In particular, the chair 14 is moveable between at least an examination position (as shown in FIGS. 1 and 4A) and a stowed position (as shown in FIGS. 2, 3, 4B, and 4C). In the examination position, the carriage 52 is positioned so the chair 14 is away from the instrument delivery stand 12 and in a position appropriate for an eye examination. For example, as shown in FIGS. 1 and 4A, in the examination position, the lower instrument arm assembly 24 is positioned so that the table 40 is positioned generally in front of where a patient would be seated in the chair 14. Examination instruments can be situated on the table 40 and used during an eye examination procedure. Also, a physician or other practitioner can readily access instruments from the instrument delivery stand 12. In the examination position, the base support covers 58a, 58b cover the chair end 72 of the base plate 54 (as shown in FIG. 1).

The chair 14 is easily moved from the examination position to the stowed position. In particular, a physician or other practitioner may push the chair 14 in the direction of the instrument delivery stand 12 and move the chair 14 until it is positioned generally adjacent the instrument delivery stand (as seen in FIG. 3). As discussed above, the track and guide assembly 60 provides for movement of the chair-supporting carriage 52 on the base plate 54, which facilitates movement of the chair 14. The physician or other practitioner might also move the lower instrument arm assembly 24, for example, so that the table 40 is moved away from the chair 12, such as by rotating the arm 36 of the lower instrument arm assembly 24 with respect to the support 38 (as shown in FIGS. 2 and 4B, and as indicated by the arrow in FIG. 1). In the stowed position, the chair end 72 of the base plate 54 extends just slightly beyond the base support cover 58b. The chair 14 is easily moved from the stowed position to the examination position, such as by reversing the steps discussed above.

When the chair 14 is moved to the stowed position, a space S is created adjacent the chair 14 (as shown in FIG. 4B). A wheelchair 138 can be positioned in the space S so that a patient seated in the wheelchair 138 is in an appropriate examination position (as shown in FIG. 4C). In particular, the lower instrument arm assembly 24 can be positioned so that the table 40 is positioned generally in front of where a patient would be seated in the wheelchair 138. Examination instruments can be situated on the table 40 and used during an eye examination procedure for the patient in the wheelchair 138. Also, a physician or other practitioner can readily access instruments from the instrument delivery stand 12. Thus, examining a patient in the wheelchair 138 in the space S would be generally similar to examining a patient seated in the chair 14 when the chair 14 is in the examination position.

Figure 5:
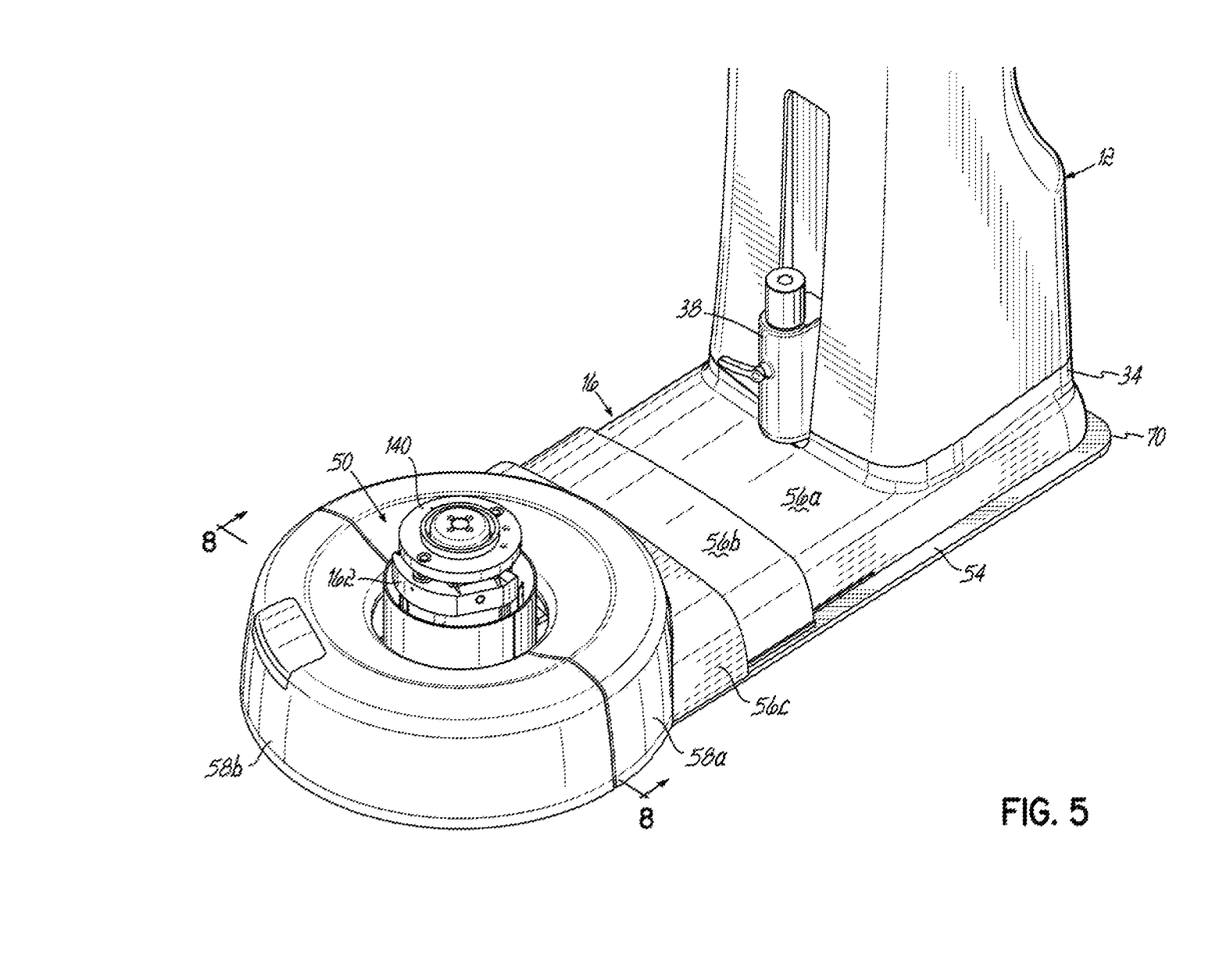
FIG. 5 is an isometric view showing features of a chair base support, a base, and an instrument delivery stand.

As mentioned above, the chair 14 is supported by the base support 50 which, in turn, is supported on the carriage 52. In particular, the base support 50 includes a chair mount disc 140 (as shown in FIGS. 5 and 6) for attaching with the chair 14. The base support 50 further includes features for raising and lowering the chair 14.

In particular, the base support 50 includes a lift mechanism 142, which includes a lift cylinder device 144. The lift cylinder device 144 is moveable up and down, and can be coupled directly with the chair mount disc 140 to raise and lower the chair 14. In the embodiment shown, however, the lift mechanism 142 further includes a lift extension assembly 146 and a pulley assembly 148 which cooperate with the lift cylinder device 144 to provide additional lift to the chair 14.

In particular, the lift extension assembly 146 includes shafts 150 that are connected at one end to a shaft hub 152 and at their other end to the chair mount disc 140. The pulley assembly 148 includes a pulley 154 mounted to the lift cylinder device 144 and a cord 156 that extends around the pulley 154 and is connected at one end to the carriage 52 and at the other to the shaft hub 152. The cord 156 can include chains, cables, belts, or any other structure appropriate for use with the pulley assembly 148.

When the lift cylinder device 144 is raised, the pulley 154 is also raised, which causes an upward force to be exerted on the shaft hub 152, which raises the shaft hub 152 relative to the pulley 154. Conversely, when the lift cylinder device 144 is lowered, the weight of the shaft hub 152 moves the shaft hub 152 away from the pulley 154 and toward the carriage 52.

In addition, the lift mechanism 142 includes an alignment assembly 160 that tends to confine the shafts 150 to vertical movement, and resists deflection of the same. In particular, the alignment assembly includes an alignment hub 162 attached to the lift cylinder device 144 and including alignment passageways 164. The alignment passageways 164 have a shape that generally corresponds with the shape of the shafts 150, and the shafts 150 extend through the alignment passageways 164. As the lift mechanism 142 raises and lowers the chair 14, the shafts 150 are moved through the alignment passageways 164, which constrain the shafts 150 to movements in generally vertical axes. The shafts 150 and the alignment passageways 164 therefore tend to resist non-vertical movement of the shafts 150, and therefore the chair mount disc 140, as the lift mechanism 142 raises and lowers the chair mount 140. The alignment passageways 164 can include bearings or other friction reducing structure for facilitating the movement of the shafts 150 in the alignment passageways 164.

Equipment for operating the lift mechanism 142 can be carried on the carriage 52, such as a motor/pump assembly 170, a hydraulic tank 172, and other related devices, the selection of which will be apparent to those interested in this art area.

Optionally, structure can be provided for locking the chair 14 in a desired position, such as in the examination or stowed positions. While not shown, it will be appreciated that the base plate 54 could include one or more locating bores for receiving a bolt or other locking structure carried by the carriage 52, for example, for engaging the locating bore and locking the chair 14 in a position relative to the base plate 54. However, because the chair 14, the base support 50, and the carriage 52 together have a substantial weight, the chair 14 will tend to stay in a position until acted on, and locking structures may be not be necessary.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

The invention claimed is:

1. An ophthalmic examination suite comprising:
a base support having a base plate;
a carriage movable linearly on the base plate;
a chair coupled to the carriage, the chair being configured to receive a seated patient thereon; and
an instrument arm assembly configured to hold an examination instrument;
wherein the carriage is configured to laterally move the chair in a substantially linear sideways direction towards an instrument delivery stand;
further wherein, the instrument arm assembly is positionable over the chair to provide the examination instrument to a location beside the chair opposite the instrument delivery stand.

2. The ophthalmic examination suite of claim 1, wherein the instrument arm assembly extends from the instrument delivery stand via an adjustable arm.

3. The ophthalmic examination suite of claim 2, wherein the instrument arm assembly further comprises a table adjustably connected to the adjustable arm via a linkage.

4. The ophthalmic examination suite of claim 1, wherein the carriage is operatively coupled to the base plate by a track and guide assembly, the track and guide assembly facilitating movement of the carriage on the base plate.

5. The ophthalmic examination suite of claim 4, further comprising a plurality of wheels connected to the carriage, wherein at least one of the plurality of wheels is configured to engage the track and guide assembly during movement of the chair sidewardly towards the instrument delivery stand.

6. The ophthalmic examination suite of claim 5, wherein at least one of the plurality of wheels rotates about a horizontal rotation axis.

7. The ophthalmic examination suite of claim 5, wherein at least one of the plurality of wheels rotates about a vertical rotation axis.

8. The ophthalmic examination suite of claim 4, further comprising a plurality of wheels connected to the carriage, wherein at least one of the plurality of wheels is configured to engage the base plate when the carriage moves the chair sidewardly towards the instrument delivery stand.

9. The ophthalmic examination suite of claim 1, further comprising a lift mechanism for raising and lowering the chair relative to the base support.

10. The ophthalmic examination suite of claim 9, wherein the lift mechanism includes a lift cylinder device cooperating with a lift extension assembly and a pulley assembly.

11. The ophthalmic examination suite of claim 1, further comprising a plurality of base covers that are configured to at least partially cover the base plate.

12. The ophthalmic examination suite of claim 11, wherein at least one of the plurality of base covers is configured to nest within a second one of the plurality of base covers.

13. A method of configuring an ophthalmic examination suite to facilitate examining a patient in a wheelchair, the ophthalmic examination suite including a base support having a base plate, a carriage movable on the base plate, an instrument arm assembly for presenting an examination instrument to a patient, and a chair coupled to the carriage, the method comprising:
creating a space lateral and adjacent to the chair by laterally sliding the carriage in a substantially linear sideways direction towards an instrument delivery stand;
moving a wheelchair into the space; and
positioning the instrument arm assembly over the chair to present an instrument in front of the wheelchair positioned in the space.

14. The method of claim 13, wherein the ophthalmic examination suite further includes a track and guide assembly for providing movement of the carriage with respect to the base plate, and wherein the method further comprises:
engaging the track and guide assembly with at least one wheel as the carriage is moved to the position generally adjacent to the instrument delivery stand.

15. The method of claim 13, wherein the ophthalmic examination suite further includes an instrument arm assembly for presenting an examination instrument to a patient, and wherein the method further comprises:
moving the instrument arm assembly away from the chair prior to moving the chair.

16. An examination suite comprising:
a base plate;
a carriage movable linearly on the base plate with a plurality of wheels;
a chair coupled to the carriage; and
an instrument arm assembly that an instrument supporting element;
wherein the carriage and chair move laterally in a substantially linear sideways direction towards the instrument arm assembly;
further wherein, the instrument supporting element is positionable over the chair to a location beside the chair opposite the instrument arm assembly;
further wherein, the carriage is operatively coupled to the base plate by a track and guide assembly, the track and guide assembly facilitating movement of the carriage on the base plate and at least one of the plurality of wheels is configured to engage the track and guide assembly during movement of the chair sidewardly towards the instrument delivery stand.

17. The examination suite of claim 16, further wherein at least one of the plurality of wheels rotates about a horizontal rotation axis and at least one of the plurality of wheels rotates about a vertical rotation axis.

18. The examination suite of claim 16, further comprising a lift mechanism for raising and lowering the chair relative to the base support.

19. The examination suite of claim 18, wherein the lift mechanism includes a lift cylinder device.

20. The examination suite of claim 19, further comprising a lift extension assembly.

* * * * *